(12) United States Patent
Deguchi et al.

(10) Patent No.: US 10,371,630 B2
(45) Date of Patent: Aug. 6, 2019

(54) INLINE CONCENTRATION METER AND CONCENTRATION DETECTION METHOD

(71) Applicants: TOKUSHIMA UNIVERSITY, Tokushima (JP); FUJIKIN INCORPORATED, Osaka (JP)

(72) Inventors: Yoshihiro Deguchi, Tokushima (JP); Masaaki Nagase, Osaka (JP); Nobukazu Ikeda, Osaka (JP); Michio Yamaji, Osaka (JP)

(73) Assignees: Tokushima University, Tokushima (JP); Fujikin Incorporated, Osaka (JP)

( * ) Notice: Subject to any disclaimer, the term of this patent is extended or adjusted under 35 U.S.C. 154(b) by 192 days.

(21) Appl. No.: 14/909,424

(22) PCT Filed: Jul. 18, 2014

(86) PCT No.: PCT/JP2014/003830
§ 371 (c)(1),
(2) Date: Feb. 1, 2016

(87) PCT Pub. No.: WO2015/015750
PCT Pub. Date: Feb. 5, 2015

(65) Prior Publication Data
US 2016/0169800 A1    Jun. 16, 2016

(30) Foreign Application Priority Data

Jul. 31, 2013    (JP) .................... 2013-159836

(51) Int. Cl.
*G01N 21/31*    (2006.01)
*G01N 21/33*    (2006.01)
(Continued)

(52) U.S. Cl.
CPC ......... *G01N 21/5907* (2013.01); *G01N 21/33* (2013.01); *G01N 2021/3148* (2013.01);
(Continued)

(58) Field of Classification Search
CPC ....... G01N 21/5907; G01N 2021/3148; G01N 2021/5969; G01N 2021/8411;
(Continued)

(56) References Cited

U.S. PATENT DOCUMENTS 3,811,776 A * 5/1974 Blau, Jr. ............ G01N 21/3518
250/343
4,926,021 A * 5/1990 Streusand ............. H01J 49/105
219/121.5
(Continued)

FOREIGN PATENT DOCUMENTS

CN    102016550 A    4/2011
JP    5-45279 A    2/1993
(Continued)

OTHER PUBLICATIONS

Search report issued in corresponding International application PCT/JP2014/003830, completed Sep. 14, 2014 and dated Sep. 30, 2014.
(Continued)

*Primary Examiner* — David P Porta
*Assistant Examiner* — Blake C Riddick
(74) *Attorney, Agent, or Firm* — Griffin and Szipl PC

(57) ABSTRACT

An inline concentration meter includes a light source unit emitting mixed light containing at least two wavelengths with a phase difference, a detecting unit including a light incident part for entering the mixed light emitted from the light source unit into a fluid passage of a detector body and at least two light detection parts receiving the mixed light passed through the fluid passage, a computing processor unit conducting frequency analyzes of detection signals of the mixed light output from the respective light detection parts and computing variations of intensities of the detection signals corresponding to absorbances in at least two fre-
(Continued)

quency ranges to compute a concentration of fluid in the fluid passage based on the variations of the intensities of the detection signals, and a recording/displaying unit recording and displaying a value of the fluid concentration computed at the computing processor unit.

16 Claims, 7 Drawing Sheets

(51) Int. Cl.
    *G01N 21/59* (2006.01)
    *G01N 21/84* (2006.01)
    *G01N 21/85* (2006.01)

(52) U.S. Cl.
    CPC ........... *G01N 2021/5969* (2013.01); *G01N 2021/8411* (2013.01); *G01N 2021/8578* (2013.01); *G01N 2201/0627* (2013.01); *G01N 2201/0691* (2013.01)

(58) Field of Classification Search
    CPC ... G01N 2021/8578; G01N 2201/0627; G01N 2201/0691
    USPC .................. 250/373, 339.13, 343, 338.5
    See application file for complete search history.

(56) References Cited

U.S. PATENT DOCUMENTS

| | | | | |
|---|---|---|---|---|
| 5,113,073 A * | 5/1992 | Szepan | ............... | G01N 21/39 250/343 |
| 5,652,431 A * | 7/1997 | Desisto | ............... | C30B 25/14 117/86 |
| 5,672,869 A * | 9/1997 | Windig | ............... | H01J 49/0036 250/282 |
| 5,693,945 A * | 12/1997 | Akiyama | ............... | G01N 21/33 250/339.13 |
| 5,751,416 A * | 5/1998 | Singh | ............... | G01J 3/30 356/300 |
| 5,770,156 A * | 6/1998 | Dosoretz | ............... | G01N 21/03 356/434 |
| 5,803,974 A * | 9/1998 | Mikoshiba | ............... | C23C 16/452 118/722 |
| 5,818,578 A * | 10/1998 | Inman | ............... | C23C 16/4412 356/246 |
| 5,949,537 A * | 9/1999 | Inman | ............... | G01N 21/031 356/246 |
| 5,963,336 A * | 10/1999 | McAndrew | ............... | C23C 16/4412 216/60 |
| 6,084,668 A * | 7/2000 | McAndrew | ............... | G01N 21/031 356/246 |
| 6,421,127 B1 * | 7/2002 | McAndrew | ............... | G01J 3/0259 356/437 |
| 6,862,535 B2 * | 3/2005 | Binder | ............... | G01J 3/453 702/24 |
| 7,570,360 B1 * | 8/2009 | Tkachuk | ............... | G01J 3/42 250/339.07 |
| 7,835,005 B2 | 11/2010 | Appel et al. | | |
| 9,651,467 B2 * | 5/2017 | Deguchi | ............... | G01N 9/00 |
| 2003/0033973 A1 * | 2/2003 | Hayashida | ............... | C01C 1/003 117/84 |
| 2006/0199546 A1 * | 9/2006 | Durgin | ............... | H04B 17/318 455/67.11 |
| 2006/0262311 A1 * | 11/2006 | Muta | ............... | G01J 3/433 356/437 |
| 2006/0290934 A1 * | 12/2006 | Boekelman | ............... | G01N 21/031 356/432 |
| 2007/0145275 A1 * | 6/2007 | Wong | ............... | G01N 21/3504 250/339.13 |
| 2007/0152237 A1 * | 7/2007 | Laforgia | ............... | G01N 21/31 257/184 |
| 2007/0241280 A1 * | 10/2007 | Dainobu | ............... | G01J 3/02 250/343 |
| 2007/0290129 A1 * | 12/2007 | Ogo | ............... | G01J 3/443 250/288 |
| 2008/0011055 A1 * | 1/2008 | Riddle | ............... | G01N 21/1702 73/24.02 |
| 2008/0035848 A1 * | 2/2008 | Wong | ............... | G01J 3/02 250/345 |
| 2009/0027654 A1 * | 1/2009 | Takahashi | ............... | G01N 21/00 356/36 |
| 2009/0213380 A1 | 8/2009 | Appel et al. | | |
| 2012/0009694 A1 * | 1/2012 | Maslar | ............... | C23C 16/45544 438/16 |
| 2012/0188550 A1 * | 7/2012 | Matsuda | ............... | G01N 21/3504 356/437 |
| 2012/0330568 A1 * | 12/2012 | Izawa | ............... | G01N 21/0303 702/24 |
| 2014/0034840 A1 * | 2/2014 | Davenport | ............... | G01J 3/42 250/370.01 |
| 2014/0091219 A1 * | 4/2014 | Schaefer | ............... | G01N 21/314 250/338.5 |
| 2015/0268159 A1 * | 9/2015 | Tabaru | ............... | G01N 21/39 356/437 |
| 2016/0061704 A1 * | 3/2016 | Deguchi | ............... | G01N 21/05 250/573 |
| 2016/0084700 A1 * | 3/2016 | Nagase | ............... | G01N 21/0303 359/894 |

FOREIGN PATENT DOCUMENTS

| | | |
|---|---|---|
| JP | 10-26584 A | 1/1998 |
| JP | 2000-206045 A | 7/2000 |
| JP | 2005-241249 A | 9/2005 |
| JP | 2010-203855 A | 9/2010 |
| JP | 2012-142355 A | 7/2012 |

OTHER PUBLICATIONS

Search report issued in corresponding Taiwanese application 103125860, dated May 4, 2015.
Masciotti, James M., et al. "Digital Lock-In Algorithm for Biomedical Spectroscopy and Imaging Instruments With Multiple Modulated Sources," Proceedings of the 28th IEEE EMBS Annual International Conference Aug. 2006, FRC05.5, pp. 3198-3210.

* cited by examiner

US 10,371,630 B2

INLINE CONCENTRATION METER AND CONCENTRATION DETECTION METHOD

This is a National Phase Application in the United States of International Patent Application No. PCT/JP2014/003830 filed Jul. 18, 2014, which claims priority on Japanese Patent Application No. 2013-159836, filed Jul. 31, 2013. The entire disclosures of the above patent applications are hereby incorporated by reference.

TECHNICAL FIELD

The present invention relates to improvements in inline concentration meters as well as concentration detection methods used for raw material fluid supply apparatuses and the like of semiconductor manufacturing equipment. More particularly, the present invention relates to an ultraviolet absorption type inline gas concentration meter and a gas concentration detection method for better sensitivity, reproducibility and measurement precision, for downsizing and space saving, and for cost reduction.

BACKGROUND ART

In raw material fluid supply apparatuses and the like of semiconductor manufacturing equipment, process gas having a stable concentration is required to be supplied to a processing device for improving quality of a semiconductor product.
Thus, in the conventional raw material fluid supply apparatuses of this kind such as a bubbling-type raw material fluid supply apparatus as shown in FIG. 7, an infrared absorption type concentration meter 22 is provided near a vaporized raw material outlet of a temperature controlled raw material tank 21, and process gas 24, e.g., process gas including vaporized organic metal raw material such as trimethylgallium (TMGa), having a predetermined raw material concentration is supplied to a reactor 23, while adjusting a temperature of the raw material tank 21, a flow rate of career gas CG, a vapor pressure Po in tank and the like based on concentration detection signals output from the concentration meter 22.
In FIG. 7, a reference sign 25 designates a thermal mass flow controller of the career gas, a reference sign 26 designates a pressure regulator of the tank pressure, a reference sign 33 designates a supply line of the career gas, a reference sign 34 designates a discharge line of exhaust gas, and a reference sign G designates raw material gas. Here, not only liquid raw material but sublimable solid raw material may be used as a source of the raw material gas included in the process gas 24.

As the infrared absorption type concentration meter 22, concentration meters with various configurations are practically used though, the inline concentration meter 22 includes a sample cell 30a through which the raw material gas G flows, a reference cell 30b through which reference gas C flows, a light source 28 that emits infrared light into the respective cells, a light quantity detector 29 for the lights that have passed through the respective cells, and a computing device (not shown) for computing a concentration of the raw material based on absorbances found from detection signals output from the detector 29 as shown in FIG. 8. Here, a reference sign A designates a preamplifier, a reference sign S designates the semiconductor manufacturing equipment, and a reference sign SC designates a light transmitting window. The light source 28 moves upwards and downwards integrally with the light receiver 29 to emit light into the sample cell 30a as well as the reference cell 30b. (Japanese Laid-Open Patent Publication No. 2000-206045)

Then in the concentration meter 22 shown in FIG. 8, the absorbance of the gas in the sample cell 30a is measured and the concentration of the gas is computed by applying the Beer-Lambert law and others to the measured absorbance. At this point, appropriate corrections for measurements including a zero point adjustment are made by sliding upwards the light source 28 and the light receiver 29 integrally and detecting the absorbance of the reference cell 30b.

However, the infrared absorption type concentration meter 22 has problems such as (I) instability of the detector 29 due to rather large fluctuations of the light source 28, (II) low responsiveness due to an absorbance averaging process that leads to relatively poor concentration detection sensitivity, and (III) increase in size as well as production cost of the detector 29 that requires the cells 30a and 30b, both of which have relatively long light paths.

Furthermore, in order to continuously conduct the stable gas concentration measurement for a long term, transparency of the light transmitting window SC needs to last for a long time, and in case the transparency changes with time, the stable gas concentration measurement becomes difficult.

For improving measurement speeds and S/N ratios or the like of infrared absorption type spectrophotometers, Fourier transform infrared (FT-IR) spectrophotometers have been developed and utilized, where non-dispersive optical systems with interferometers are used instead of dispersion type optical systems with diffraction gratings and/or slits to detect all wavelengths simultaneously and calculate a luminous intensity of each wavelength component by applying Fourier transformation to the detected values.

However, even in the concentration meter with the FT-IR spectrophotometers, the problems of the poor measurement precision and low reproducibility due to fluctuations of the light source are left unsolved because wavelength regions for measurement are basically equal to an infrared region.

Frequency ranges for measurement may be expanded to from far infrared to visible light by changing light sources, beam splitters, detectors, light transmitting windows and the like, though it is actually difficult to implement the spectrum expansion due to troubles for exchanges of the components and/or various problems due to the infrared system.

On the other hand, gas concentration meters using ultraviolet light have been developed for solving the problems including poor responsiveness and/or low measurement precision in the infrared absorption method.

FIG. 9 illustrates a configuration outline of the device, and a light source 28 includes a light source unit 28a having an ultraviolet light lamp that emits ultraviolet light with wavelengths of 200 to 400 nm (for example, a deuterium lamp and Hg—Xe lamp) and a spectroscope 28b.

In other words, as shown in FIG. 9, the gas concentration meter includes a sample cell 30a through which raw material gas G flows, a reference cell 30b through which reference gas C flows, the light source unit 28a and the spectroscope 28b that emit ultraviolet light into the respective cells, a light quantity detector 29 for the lights that have passed through the respective cells, and a computing device (not shown) for calculating a concentration of the raw material based on absorbances found from detection signals which are output from 29a of the detector. Here, a reference sign 31 designates a gas purification device, a reference sign 32 designates a pump, a reference sign 35 designates an exhaust gas treatment device, a reference sign M designates a mirror, a reference sign MP designates a diffraction grating, a reference sign ML designates a slit, a reference sign MS designates a sector mirror, and a reference sign MG designates a grating mirror. (Japanese Laid-Open Patent Publication No. 2005-241249)

In the ultraviolet light gas concentration meter, even though the absorbance of the reference cell 30b is detected with the double-beam type spectroscope 28b to conduct appropriate corrections of measurement values including a zero point adjustment, the problems of the large fluctuations of the light source 28 and relatively poor responsiveness as well as detection sensitivity are still left unsolved because a basic configuration of an optical system is exactly the same as in the case of the infrared absorption type concentration meter.

As described above, in case the conventional infrared absorption type or ultraviolet absorption type concentration meter is used, not only a problem of difficulties in downsizing and/or cost reduction of the equipment but many other problems that need to be fundamentally resolved quickly are left unsolved in responsiveness, detection sensitivity, detection precision, and reproducibility of the concentration measurement as well as in maintenance of airtightness and purity of the gas and so on.

CITATION LIST

Patent Literature

Patent Document 1: Japanese Laid-Open Patent Publication No. 2000-206045
Patent Document 2: Japanese Laid-Open Patent Publication No. 2005-241249

SUMMARY OF INVENTION

Technical Problem

Principal objects of the present invention are to provide an ultraviolet light absorption type inline concentration meter which is smaller-sized and may be produced cheaper for stable concentration measurement with high responsiveness, high sensitivity, and high precision for a long period even in case raw material gas is highly corrosive organic raw material gas, and to provide a method for measuring a concentration with the meter for solving previously described problems of raw material gas concentration meters used in conventional raw material fluid supply apparatuses and the like and/or concentration measurement methods with the meters: (I) simplification of a configuration, downsizing, and product cost reduction of the concentration meter may not be easily achieved; (II) responsiveness and sensitivity of concentration measurement are low; (III) measurement reproducibility is poor and the concentration measurement of the raw material gas may not be conducted steadily and precisely; and (IV) measurement precision can be easily lowered as transparency of a light transmitting window changes.

Solution to Problem

According to a first embodiment of the present invention, a concentration meter basically includes a light source unit for emitting mixed light containing at least two wavelengths with a phase difference, a detecting unit that includes a light incident part for entering the mixed light emitted from the light source unit into a fluid passage of a detector body and at least two light detection parts for receiving the mixed light passed through the fluid passage, a computing processor unit for conducting frequency analyses of detection signals of the mixed light output from the respective light detection parts and computing variations of intensities of the detection signals corresponding to absorbances in the at least two frequency ranges to compute a concentration of fluid in the fluid passage based on the variations of the intensities of the detection signals in the at least two frequency ranges, and a recording/displaying unit for recording and displaying a value of the fluid concentration computed at the computing processor unit.

According to a second embodiment of the present invention, in the first embodiment, the light source unit emits mixed light containing three wavelengths.

According to a third embodiment of the present invention, in the first embodiment, the light source unit has an LED or laser diode.

According to a fourth embodiment of the present invention, in the first embodiment, the light source unit emits ultraviolet light in a wavelength region of 200 to 400 nm.

According to a fifth embodiment of the present invention, in the first embodiment, the computing processor unit conducts frequency analyses through Fourier transformation or wavelet transformation.

According to a sixth embodiment of the present invention, in the first embodiment, the computing processor unit computes a concentration of organic metal raw material gas included in the mixed gas flowing in the fluid passage.

According to a seventh embodiment of the present invention, in the first embodiment, the detecting unit has one light incident part and two light detection parts.

According to an eighth embodiment of the present invention, in the first embodiment, the light source unit emits mixed ultraviolet light containing three wavelengths.

According to a ninth embodiment of the present invention, in the first embodiment, the computing processor unit conducts frequency analyses of detection signals of the mixed light containing the three wavelengths through Fourier transformation.

According to a tenth embodiment of the present invention, in the seventh embodiment, the one light incident part is arranged on one side of the detector body and the two light detection parts are arranged on other one side opposing to the one side.

According to an eleventh embodiment of the present invention, in the second embodiment, the one light incident part is arranged on one side of the detector body and three light detection parts are arranged on other one side opposing to the one side.

According to a twelfth embodiment of the present invention, in the seventh embodiment, the one light incident part and one light detection part are arranged on one side of the detector body and the two light detection parts are arranged on other one side opposing to the one side.

According to a thirteenth embodiment of the present invention, in the first embodiment, the light source unit emits mixed light that a beam combiner provides by combining ultraviolet lights that have different wavelengths.

According to a fourteenth embodiment of the present invention, a gas concentration detection method including the steps of: entering mixed light of three ultraviolet lights having different wavelengths with phase differences emitted from a light source unit from one light incident part arranged on a detector body with a fluid passage into the fluid passage, detecting the respective ultraviolet lights that have passed through the fluid passage with at least two light detection parts arranged on the detector body, conducting frequency analyses of detection signals of the mixed light that are detected by the light detection parts through Fourier transformation or the like, computing variations of intensities of the detection signals detected by the light detection parts corresponding to absorbances in three frequency ranges, and computing a concentration of organic metal material gas included in mixed gas that flows through the fluid passage based on the at least six computed variations of the intensities of the detection signals in the three frequency ranges.

According to a fifteenth embodiment of the present invention, in the fourteenth embodiment, the number of the light detection parts is three and the concentration of the organic metal material gas included in the mixed gas that flows through the fluid passage is computed based on at least nine computed variations of intensities corresponding to the absorbances.

According to a sixteenth embodiment of the present invention, in the fourteenth embodiment, the mixed light entering from the light incident part is detected by the one light detection part and reflected light from the light detection part is entered to the another light detection part.

According to a seventeenth embodiment of the present invention, in the fourteenth embodiment, the mixed light entering from the light incident part is dispersed and entered to the two light detection parts.

Advantageous Effects of Invention

According to the present invention, a concentration meter includes:
a light source unit for emitting mixed light containing at least two wavelengths with a phase difference;
a detecting unit that includes a light incident part for entering the mixed light emitted from the light source unit into a fluid passage of a detector body and at least two light detection parts for receiving the mixed light passed through the fluid passage;
a computing processor unit for analyzing detection signals of the mixed light output from the respective light detection parts and computing variations of intensities of the detection signals corresponding to absorbances in at least two frequency ranges to compute a concentration of fluid in the fluid passage based on the variations of the intensities of the detection signals in the at least two frequency ranges; and
a recording/displaying unit for recording and/or displaying a value of the fluid concentration computed by the computing processor unit.

As a result, the intensity variation of the mixed light containing the at least two wavelengths with the phase difference between when the light enters and after the light is absorbed is firstly detected by the at least two light detection parts, and frequency analyses of the detection values corresponding to the intensity variations of the mixed light detected by the respective light detection parts are conducted to find values corresponding to the absorbances in the at least two frequency ranges, and then the concentration of the fluid is computed based on the at least six computed absorbances.

Not like conventional dispersion type optical systems that use diffraction gratings and/or slits, this allows drastic simplification of an optical system configuration which leads to significant size reduction of the device.

Additionally, by using an LED or laser diode in the light source unit, power consumption is significantly reduced and the light source life is greatly extended compared with conventional infrared light sources. Those features offer a huge advantage in practical use and allow us to easily obtain ultraviolet lights with different wavelengths.

Furthermore, because at least two ultraviolet lights having different wavelengths with a phase difference are used and the absorbances are measured with the at least two light detection parts, high measurement accuracy as well as measurement reproducibility become possible, and stable concentration measurement also becomes possible as so-called fluctuations of the light source is almost completely eliminated.

In addition, because the detecting unit includes the detector body that has the fluid passage and the light incident part as well as the light detection parts on side faces thereof, the detecting unit may be substantially downsized and its installation to a pipeline as well as removal from the pipeline may be easily conducted.

DESCRIPTION OF EMBODIMENTS

Hereinafter, embodiments of the present invention are described with reference to the drawings.

Figure 1:
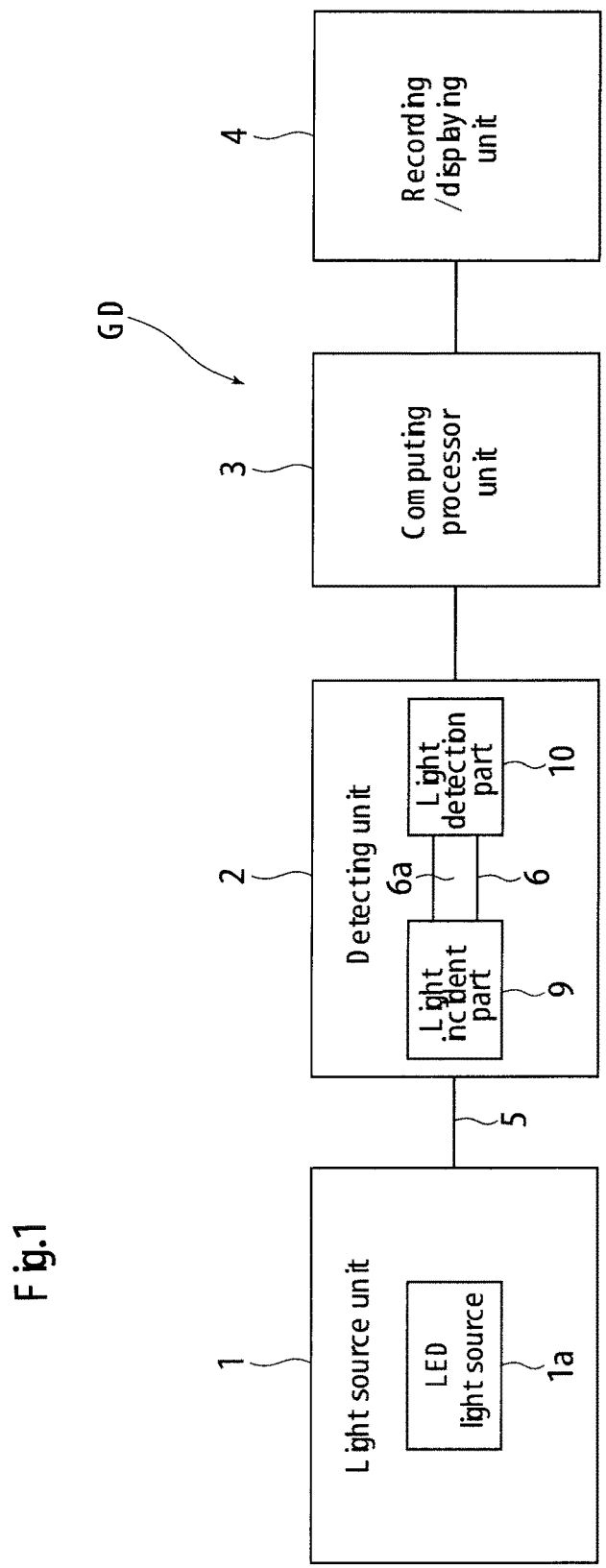
FIG. 1A schematic diagram showing a configuration of a raw material fluid concentration meter of an embodiment of the present invention.

FIG. 1 is a schematic diagram showing a configuration of a raw material fluid concentration meter of an embodiment of the present invention.

A raw material gas concentration meter GD according to the present invention includes a light source unit 1 with an LED light source 1a, a detecting unit 2 that has a light incident part 9, a detector body 6 with a fluid passage 6a, and light detection parts 10, a computing processor unit 3 as well as a recording/displaying unit 4. Here the detecting unit 2 is formed for inline installation in a pipeline as described later.

Figure 2:
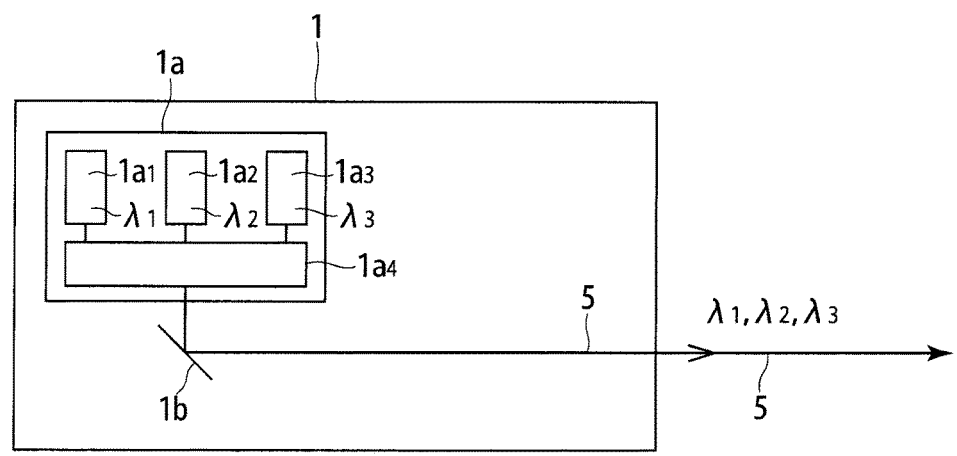
FIG. 2A schematic diagram of a configuration of a light source unit.

In other words, three ultraviolet lights having different wavelengths are emitted from the light source unit 1 with different phases and entered to a beam combiner $1a_4$ (FIG. 2). The respective ultraviolet lights entered are mixed in the beam combiner $1a_4$ and then the mixed light is entered to the light incident part 9 of the detecting unit 2 through an optical fiber 5.

The ultraviolet light entered to the light incident part 9 of the detecting unit 2 runs through raw material gas G in the fluid passage 6a, and is detected by the light detection parts 10 provided to at least two different locations.

In the embodiment, as described later based on FIGS. 2 to 5, the three ultraviolet lights having wavelengths of $\lambda_1$, $\lambda_2$, and $\lambda_3$ with the phase differences are emitted from the LED light source 1a and the mixed light of the three ultraviolet lights is entered to the one light incident part 9, then the ultraviolet light radiated into the fluid gas G from the light incident part 9 is detected by the two light detection parts 10 to detect so-called absorbances of the ultraviolet light. Here, to the second light detection part, reflected light from a sapphire made light transmitting window 9a of the first light detection part is entered.

Here, although not shown in the drawings, the entered light may be dispersed from the one light incident part 9 and the mixed light may be directly entered to the at least two or more light detection parts 10.

The light detection values (light reception values) of the mixed light (synthesized light) containing the three wavelengths of $\lambda_1$, $\lambda_2$, and $\lambda_3$ detected by the two light detection parts 10a and 10b are separately input to the computing processor unit 3 for frequency analyses through Fourier transformation and the like to compute intensities of the light detection values of the three frequency range components, and values corresponding to total six absorbances (two light detection parts×three frequency ranges) are found.

Then eventually, a concentration of the raw material gas that passes in the fluid passage 6a is computed and displayed based on a matrix of the computed values corresponding to the six absorbances.

Referring to FIG. 2, the light source unit 1 includes the multi LED light source 1a, the beam combiner 1$a_4$, a reflect mirror 1b, and the optical fiber 5. The three types of ultraviolet lights respectively having the wavelengths of $\lambda_1$, $\lambda_2$, and $\lambda_3$ are emitted from the multi LED light source 1a and the ultraviolet lights are combined by the beam combiner 1$a_4$ into the one light to be entered to the detecting unit 2 via the reflect mirror 1b and the optical fiber 5.

Here in the embodiment shown in FIG. 2, phase differences φ are given between the respective ultraviolet lights by differentiating light emission start times of respective LED light sources 1$a_1$, 1$a_2$, and 1$a_3$, though the ultraviolet lights may be simultaneously emitted from the LED light sources 1$a_1$, 1$a_2$, and 1$a_3$ with the phase differences φ between the respective ultraviolet lights given by a phase adjuster (not shown) that is separately provided.

So-called a multi LED is used as the LED light source 1a, and specifically, a small-sized tri-color high-luminance LED in a wavelength region of 200 nm to 400 nm is used in the embodiment.

Here in the implementation examples shown in FIGS. 1 and 2, the LED is used as the light source, though a so-called LD (laser diode), which is included in a group of LEDs, may, of course, be used as the light source.

Figure 3:
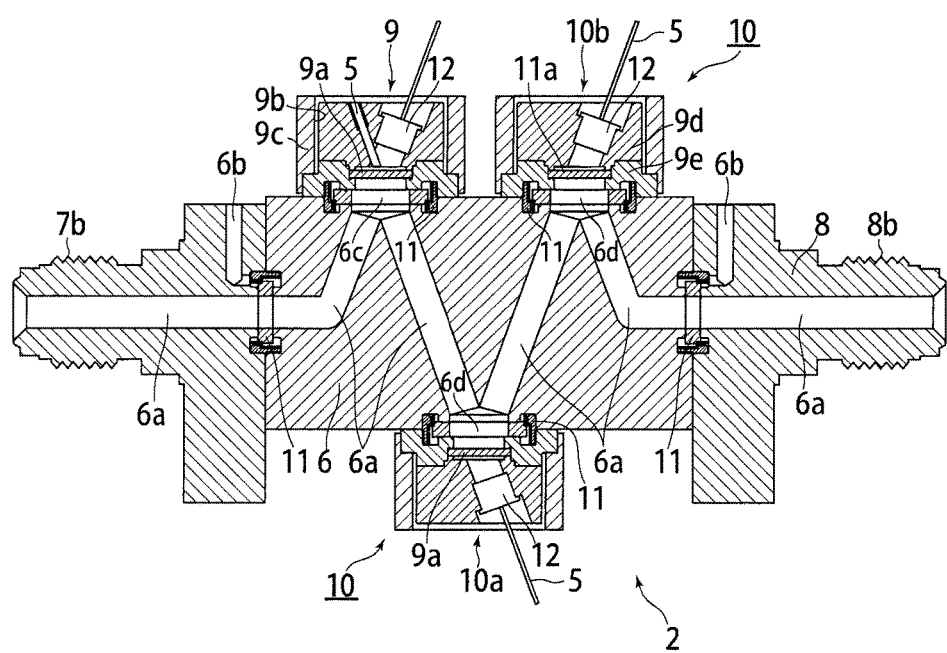
FIG. 3A longitudinal partial view of a configuration of a detecting unit.

As shown in FIG. 3, the detecting unit 2 includes the detector body 6, the one light incident part 9, and the two light detection parts 10a and 10b.

The detector body 6 is made of stainless steel and the fluid passage 6a is arranged therein. Further, an inlet block 7 as well as an outlet block 8 are airtightly fixed to each side of the detector body 6 via gasket-type seals 11 with bolts (not shown). Here, a reference sign 6b designates a leakage inspection hole, a reference sign 6c designates a fixation hole for the light incident part 9, and a reference sign 6d designates fixation holes for the light detection parts 10.

The light incident part 9 is arranged on a top face of the detector body 6 and the light detection parts 10a and 10b are respectively arranged on the top face and a down face of the detector body 6 to obliquely face each other. The mixed light of the three ultraviolet lights respectively having the wavelengths of $\lambda_1$, $\lambda_2$, and $\lambda_3$ with the phase differences φ is entered to the sapphire made light transmitting window 9a in the light incident part 9 from the light source unit 1 via the optical fiber 5.

Most of the entered mixed light is entered to the fluid passage 6a through the sapphire made light transmitting window 9a, though part of the incident mixed light is reflected by the sapphire made light transmitting window 9a, and intensity of the reflected light is detected by photo diodes 12 to be used for detection of so-called fluctuations of the light source or the like.

The light incident part 9 is arranged to obliquely face to the first light detection part 10a, and most of the light entered from the light incident part 9 is entered to the photo diode 12 in the first light detection part 10a through the fluid gas G in the fluid passage 6a as well as the sapphire made light transmitting window 9a of the first light detection part 10a for light intensity detection of the entered light.

Here, since the mixed light is entered to the sapphire made light transmitting window 9a in the first light detection part 10a at a certain angle of inclination, part of the mixed light is reflected here and the reflected light from the first light detection part 10a is entered to the second light detection part 10b on the top face through the fluid passage 6a.

Respective light intensities of the mixed light containing the wavelengths of $\lambda_1$, $\lambda_2$, and $\lambda_3$ detected by the light detection parts 10a and 10b change depending on light absorption by the raw material fluid G (process fluid) flowing in the fluid passage 6a. In other words, the respective light intensities vary by the concentration of the raw material gas G and the like.

Here, the respective light intensity signals detected by the photo diodes 12 are input to the computing processor unit 3 which is described later and the concentration of the raw material gas G is automatically computed therein.

The light incident part 9 and the light detection parts 10a as well as 10b have completely the same configuration, and as shown in FIG. 3, each includes a holding-fixing body 9c with a flange reception hole 9b at a center thereof, a first fixation flange 9d and a second fixation flange 9e that are arranged on an outer surface of the detector body 6, the sapphire made light transmitting panel 9a airtightly inserted and fixed between the both flanges 9d and 9e, and the photo diode 12 that is located at an upper side of the light transmitting board 9a and fixed to the first fixation flange 9d.

In other words, the second fixation flange 9e and the first fixation flange 9d are airtightly integrated by pressing a protrusion of the first fixation flange 9d into a recession of the second fixation flange 9e with the sapphire made light transmitting panel 9a inserted and fixed therebetween.

The second fixation flange 9e and the first fixation flange 9d integrated together are inserted to the flange reception hole 9b of the holding-fixing body 9c, and the holding-fixing body 9c is pressed and fixed to the detector body 6 via the gasket-type seal 11 with a fixing bolt (not shown) to airtightly fix the light incident part 9 and the light detection parts 10a and 10b to the detector body 6.

In FIG. 3, reference signs 7b and 8b designate coupling parts, the reference sign 6b designates the leakage inspection hole, the reference sign 6c designates the fixation hole for the light incident part 9, and the reference sign 6d designate the fixation holes for the light detection parts 10a and 10b. The light incident part 9 and the light detection parts 10a as well as 10b are fixed with fixing bolts (not shown).

In the embodiment shown in FIG. 3, the light incident part 9 is arranged on the top face of the detector body 6 and the light detection parts 10 are respectively arranged on the top face and the down face of the detector body 6, though the light incident part 9 and the light detection parts 10 may be arranged in a row on one same face.

Additionally, in the embodiment shown in FIG. 3, the number of the light detection parts 10 is two, though the number of the light detection parts may, of course, be three or even four. However, the most proper number of the light detection parts 10 should be two to three in regards to measurement precision and a cost of the concentration meter.

The light intensities detected by the respective light detection parts 10a and 10b on the top face vary by length of a light path in the fluid passage 6a, the concentration of the raw material gas G and the like, and the detected light intensity signals corresponding to the absorbances are input to the computing processor unit 3 for computing the concentration of the raw material in the raw material fluid.

Figure 4:
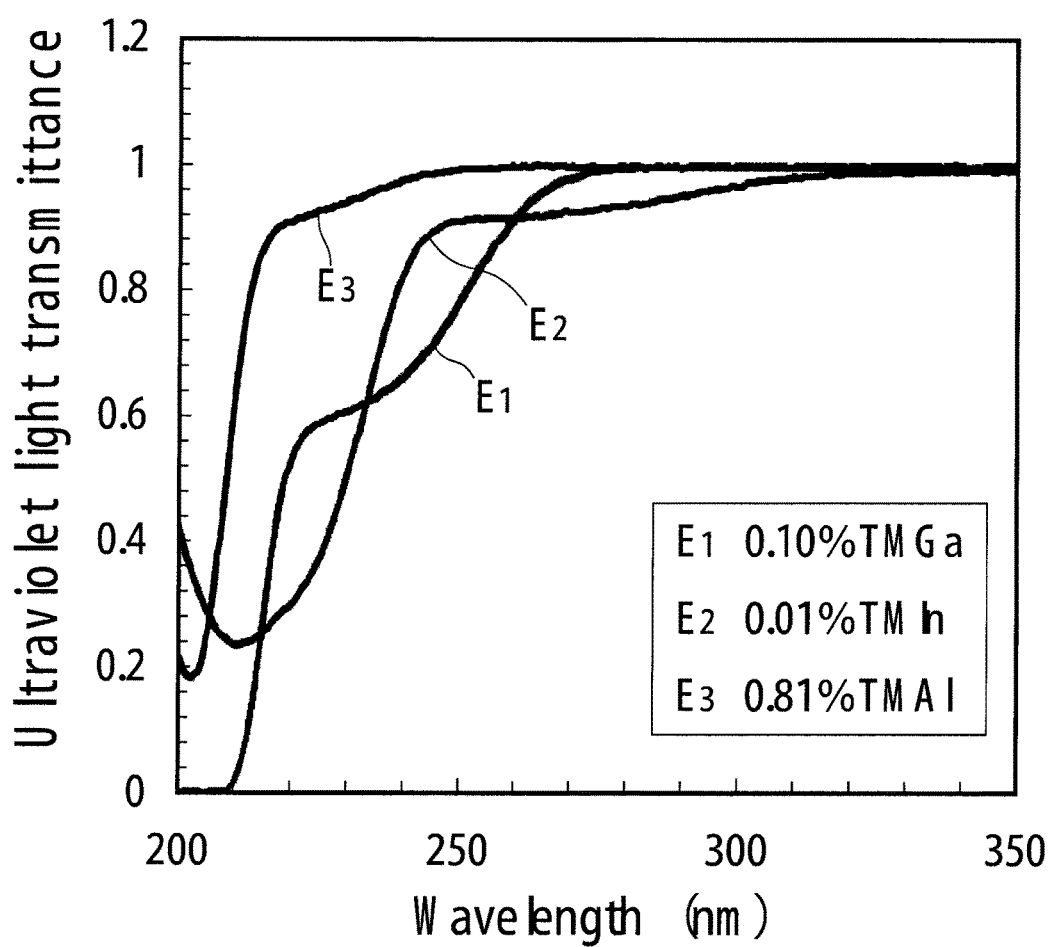
FIG. 4A graph showing examples of ultraviolet light absorption (transmittance) characteristics of organic metal raw material gases.

FIG. 4 shows examples of ultraviolet light absorption (transmittance) characteristics of organic metal raw material gases to ultraviolet light with wavelengths of 200 nm to 350 nm. In FIG. 4, a curve $E_1$, a curve $E_2$, and a curve $E_3$ respectively indicate the ultraviolet light transmittance of 0.10% TMGa gas, 0.01% TMIn gas, and 0.81% TMAl gas.

Here, the concentration Cd of the raw material may basically be computed by the following formula (1) based on the absorbance A obtained by the spectrophotometer.

$$A = \log_{10}(I_0/I) = \varepsilon \times Cd \times l \quad \text{Formula (1):}$$

In the formula (1), $I_0$ represents the intensity of the light entered from the light incident part 9, I represents the intensity of the transmitted light (intensity of the light entered to the photo diode 12 of the light detection part 10), ε represents molar absorbance coefficient of the raw material, Cd represents the raw material concentration, and A represents the absorbance.

Figure 5:
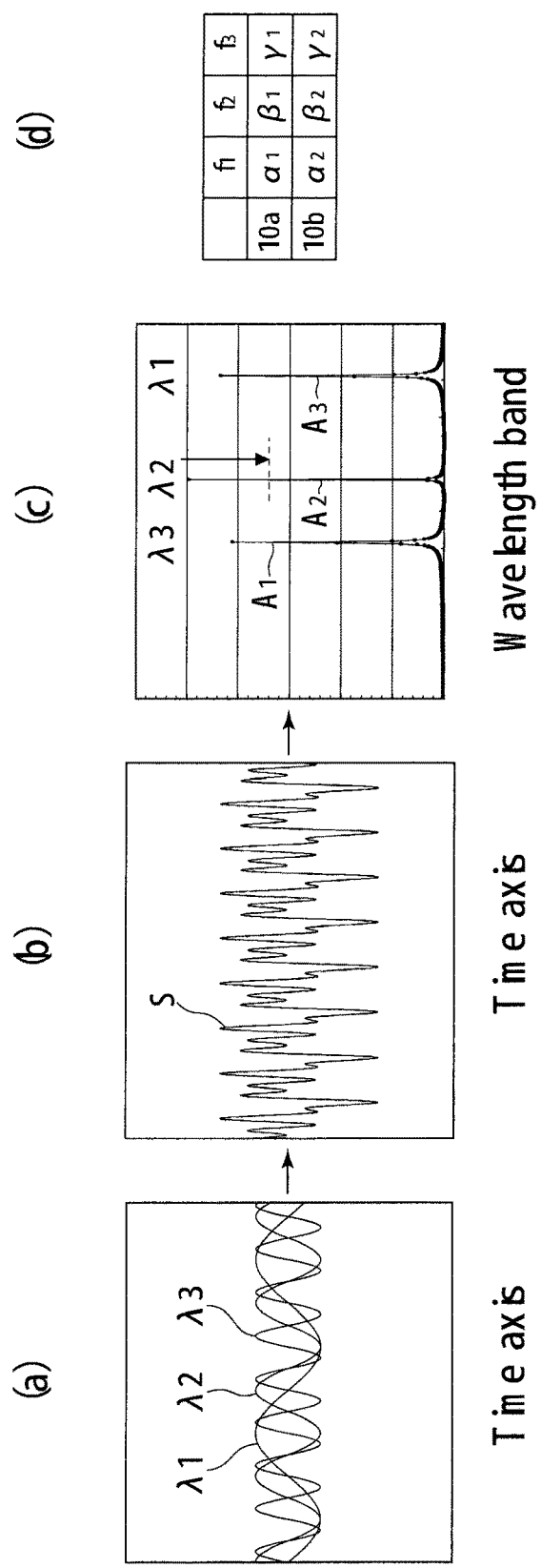
FIG. 5 (a) to (c) are explanatory diagrams of detection value processing in a computing processor unit, and (d) is an explanatory diagram of computed light absorption matrixes $\alpha$, $\beta$, and $\gamma$.

Referring to FIG. 5 (a), the mixed light of the three types of ultraviolet lights respectively having the wavelengths of $\lambda_1$, $\lambda_2$, and $\lambda_3$ with the phase differences φ is entered to the light incident part 9 of the detecting unit 2 and then radiated into the raw material gas G from the light incident part 9.

The three types of ultraviolet lights having the wavelengths of $\lambda_1$, $\lambda_2$, and $\lambda_3$ with the phase differences φ that have passed through the raw material gas G are intensity-modulated and the three lights are mixed by the beam combiner $1a_4$. Then the mixed light reaches to the light detection parts 10a and 10b. While passing through the raw material gas G, a certain wavelength of the mixed incident light is absorbed by the gas G, and the intensity of the mixed light entered to the light detection parts is detected by the respective photo diodes 12. FIG. 5 (b) shows an example of the detection value of the light intensity. Change of the intensity is measured after the absorption of the light by the organic raw material gas.

Here, the light intensities of the mixed light after the absorption of the light detected by the respective light detection parts 10a and 10b vary depending on the location of the detection of the light, the wavelength of the light, the concentration of the raw material gas, length of the transmitted light path and the like, and the detection value draws a curb like a curb S in the graph of FIG. 5 (b).

The respective detection value S of light intensities detected by the light detection parts 10a and 10b are input to the computing processor unit 3, and then frequency analyses through fast Fourier transformation and/or computing analyses of the intensities in the three frequency ranges (i.e. intensities corresponding to the absorbances) are conducted for computing the concentration of the raw material gas by applying Beer-Lambert law.

FIG. 5 (c) is a graph showing variations of the intensities of the ultraviolet lights having the wavelengths of $\lambda_1$, $\lambda_2$, and $\lambda_3$ in the three frequency ranges which are examples of the intensities corresponding to the absorbances that are basis for computation of the raw material concentration.

Subsequently, from the results of the frequency analyses through FFT (fast Fourier transformation) and/or the computed results of the variations of the light intensities corresponding to the absorbances in the respective frequency ranges (the three frequency ranges in the embodiment), the respective light absorption matrixes α, β, and γ shown in FIG. 5 (d) are obtained in the computing processor unit 3, and then the concentration of the raw material gas G is continuously computed in real time based on the light absorption matrixes α, β, and γ by using a prepared algorithm for computing the raw material gas concentration.

Adjustment of a zero point and diagnosis of abnormality, for example, detection of fogging of the sapphire made light transmitting window 9a, of the concentration meter are also conducted based on the changes of the light absorption matrixes shown in FIG. 5 (d). It has been confirmed that the present invention may realize higher measurement precision as well as measurement reproducibility, significantly reduce time required for concentration measurement, and lower a cost of the device comparing with conventional gas analyzers for $F_2$ gas using ultraviolet light.

Figure 6:
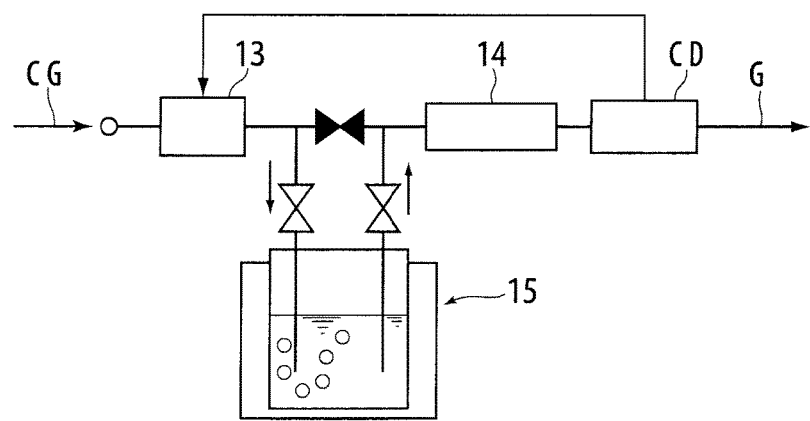
FIG. 6 A diagram showing an application example of the gas concentration meter of the present invention.

FIG. 6 shows an application example of the gas concentration meter GD according to the present invention, and the concentration of the raw material gas G is maintained at a certain level by feedback-controlling a tank pressure regulator 13 and/or a mass flow controller 14 of career gas CG based on the detection value of the concentration detected by the gas concentration meter GD.

Figure 7:
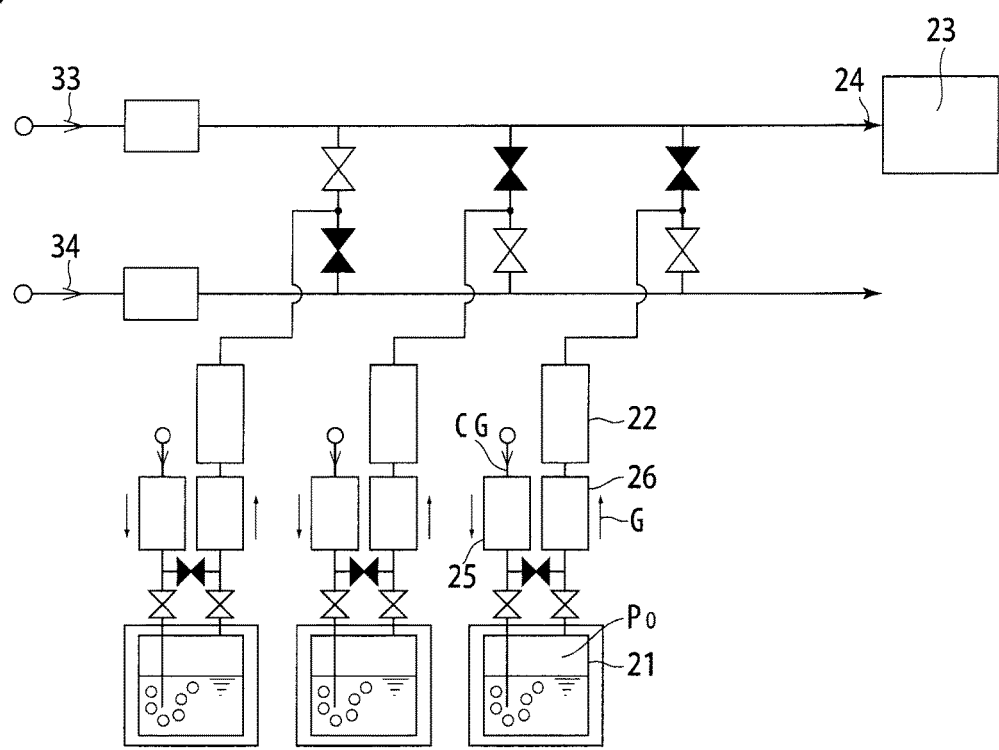
FIG. 7 A diagram showing an application example of a conventional inline gas concentration meter.
Figure 8:
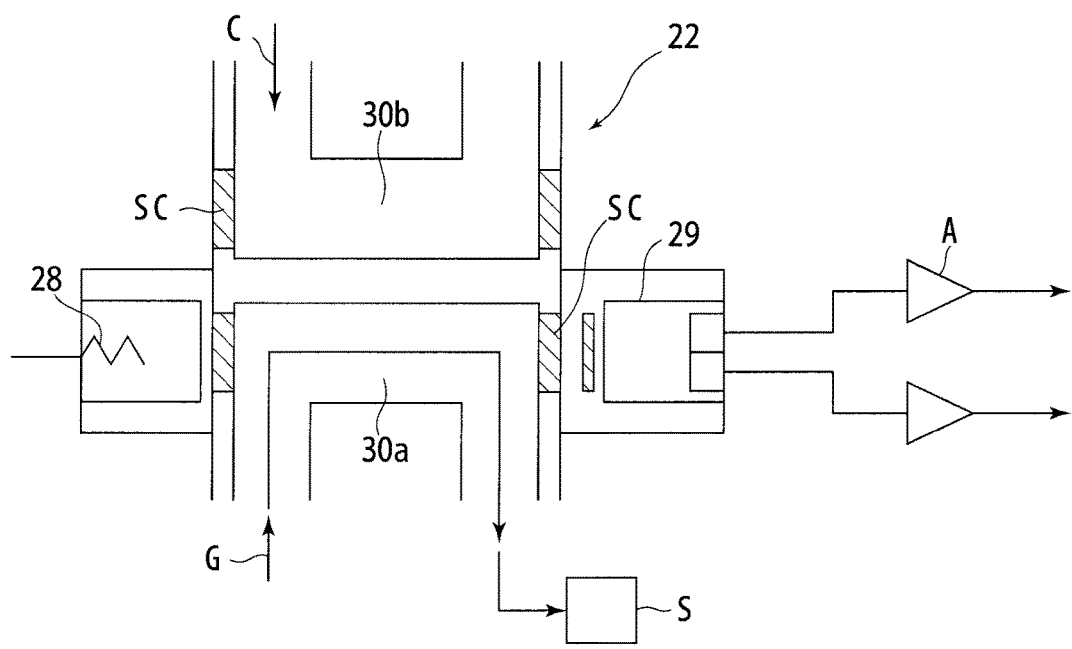
FIG. 8 A schematic diagram of a configuration of the conventional inline gas concentration meter.
Figure 9:
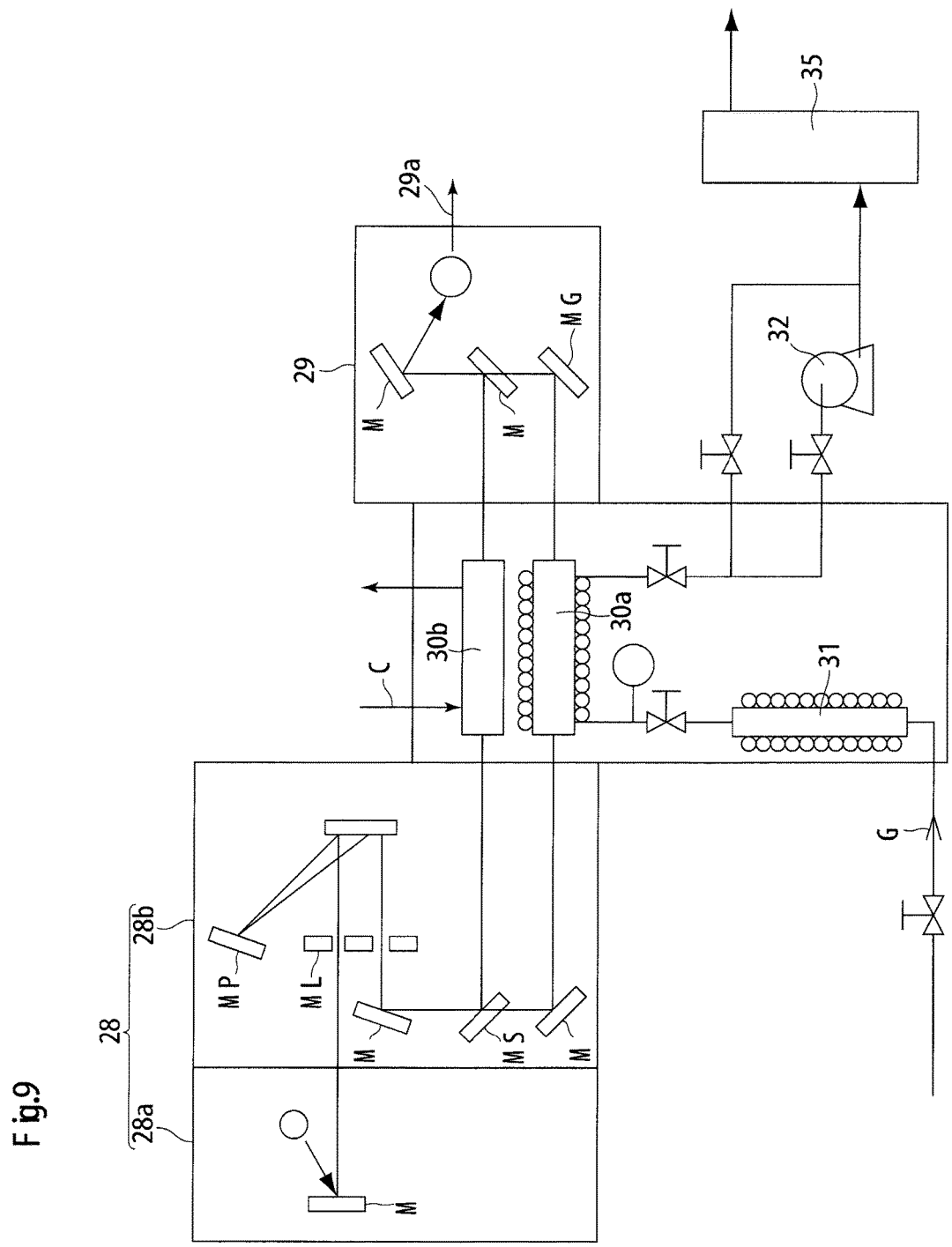
FIG. 9 A schematic diagram of a configuration of a conventional ultraviolet absorption type gas concentration meter.

Here, because a structure of a raw material gas generator 15 is almost the same as in the case of the conventional technology shown in FIG. 7, description of the structure is omitted herein.

INDUSTRIAL APPLICABILITY

A concentration meter according to the present invention may continuously detect a concentration of raw material fluid in a pipeline regardless of an original form, such as liquid or sublimable solid, of the raw material as long as the fluid has a light absorption characteristic, particularly an ultraviolet light absorption characteristic, and may be used for continuous fluid concentration detection not only in gas supply systems for semiconductor manufacturing but also in any fluid-supply pipelines and/or fluid-use apparatuses that are used with precipitating fluids, photoreactive fluids and/or corrosive fluids.

A REFERENCE SIGNS LIST 1 light source unit
1a LED light source
$1a_1$ to $1a_3$ LED light source
$1a_4$ beam combiner
1b reflect mirror
2 detecting unit
3 computing processor unit
3a fluid passage
3b coupling part 4 recording/displaying unit
5 optical fiber
6 detector body
6a fluid passage
6b leakage inspection hole
6c light incident part fixation hole
6d light detection part fixation hole
7 inlet block
8 outlet block
9 light incident part
9a sapphire made light transmitting window
9b flange reception hole
9c holding-fixing body
9d first fixation flange
9e second fixation flange
10 light detection part
10a and 10b light detection part
11 gasket-type seal
12 photo diode
13 tank pressure regulator
14 mass flow controller
15 gas generator
GD gas concentration meter
φ phase difference
$\lambda_1$ to $\lambda_3$ wavelength
S curb of light intensity detected by light detection part
E1 to E3 curb of ultraviolet light transmittance of organic raw material
$A_1$ to $A_3$ light intensity variation of ultraviolet light with wavelength of $\lambda 1$ to $\lambda 3$
α, β, γ light absorption matrix

The invention claimed is:

1. An inline concentration meter, comprising:
a light source unit for emitting mixed light having at least two wavelengths with a phase difference;
a detecting unit including a light incident part for entering the mixed light emitted from the light source unit into a fluid passage of a detector body and at least first and second light detection parts for receiving the mixed light emitted into the fluid passage, wherein a first light path through the fluid passage is defined between the light source and the first light detection part, and a second light path through the fluid passage, longer than the first light path, is defined between the light source and the second light detection part; wherein the second light path includes a first portion including the first light path and a second portion defined through the fluid passage between the first light detection part and the second light detection part;
a computing processor unit for conducting frequency analyses of detection signals of the mixed light output from the respective light detection parts and computing variations of intensities of the detection signals corresponding to absorbances in at least two frequency ranges to compute a concentration of fluid in the fluid passage based on the variations of the intensities of detection signals in the at least two frequency ranges;
wherein, from results of the frequency analyses through FFT (fast Fourier transformation) and/or the computed results of the variations of the light intensities corresponding to the absorbances in the respective frequency ranges, respective light absorption matrixes are obtained in the computing processor unit, and then the concentration of the raw material gas is continuously computed in real time based on the light absorption matrixes by using an algorithm for computing the raw material gas concentration; and
a recording/displaying unit for recording and displaying a value of the fluid concentration computed at the computing processor unit;
wherein, the light source unit emits ultraviolet light in a wavelength region of 200 nm to 400 nm; and
wherein part of the mixed light is entered into the first light detection part through a light transmitting window of the first light detection part and part of the mixed light reflected on the light transmitting window is entered into the second light detection part.

2. The inline concentration meter according to claim 1, wherein the light source unit emits mixed light containing three wavelengths.

3. The inline concentration meter according to claim 2, wherein the one light incident part is arranged on one side of the detector body and three light detection parts are arranged on another side opposing to the one side.

4. The inline concentration meter according to claim 1, wherein the light source unit has an LED or laser diode as a light source.

5. The inline concentration meter according to claim 1, wherein the computing processor unit conducts the frequency analyses through Fourier transformation or wavelet transformation.

6. The inline concentration meter according to claim 1, wherein the computing processor unit computes a concentration of organic metal raw material gas included in the mixed gas flowing in the fluid passage.

7. The inline concentration meter according to claim 1, wherein the detecting unit comprises one light incident part and the first and second light detection parts.

8. The inline concentration meter according to claim 7, wherein the one light incident part is arranged on one side of the detector body and the first and second light detection parts are arranged on another side opposing to the one side.

9. The inline concentration meter according to claim 7, wherein the one light incident part and the second light detection part are arranged on one side of the detector body and the first light detection part is arranged on another side opposing to the one side.

10. The inline concentration meter according to claim 1, wherein the light source unit emits mixed ultraviolet light of three ultraviolet lights with different wavelengths.

11. The inline concentration meter according to claim 1, wherein the computing processor unit respectively conducts frequency analysis of detection signals of mixed light containing three wavelengths through Fourier transformation.

12. The inline concentration meter according to claim 1, wherein the light source unit emits mixed light that a beam combiner provides by combining ultraviolet lights with different wavelengths.

13. A concentration detection method comprising the steps of:
entering mixed light of three ultraviolet lights having different wavelengths with phase differences, emitted from a light source unit from one light incident part arranged on a detector body with a fluid passage, into the fluid passage;
detecting the respective three ultraviolet lights passed through the fluid passage by at least first and second light detection parts arranged on the detector body, wherein a first light path through the fluid passage is defined between the light source and the first light detection part, and a second light path through the fluid passage, longer than the first light path, is defined between the light source and the second light detection part, wherein the second light path includes a first portion including the first light path and a second portion defined through the fluid passage between the first light detection part and the second light detection part;

conducting frequency analyses of detection signals of the mixed light detected by the respective light detection parts;

computing variations of intensities of the detection signals detected by the light detection parts corresponding to absorbances in three frequency ranges; and computing a concentration of organic metal material gas included in mixed gas that flows through the fluid passage based on the at least six computed variations of the intensities of the detection signals in the three frequency ranges.

14. The concentration detection method according to claim 13, wherein the number of the light detection parts is three and the concentration of the organic metal material gas included in the mixed gas that flows through the fluid passage is computed based on nine computed variations of intensities corresponding to the absorbances.

15. The concentration detection method according to claim 13, wherein the mixed light entering from the light incident part is detected by the first light detection part and reflected light from the first light detection part is entered to the second light detection part.

16. The concentration detection method according to claim 13, wherein the mixed light entering from the light incident part is dispersed and entered to the first and second light detection parts.

* * * * *